(12) United States Patent
Carlson et al.

(10) Patent No.: US 6,258,603 B1
(45) Date of Patent: Jul. 10, 2001

(54) LIGANDS FOR MODULATING THE EXPRESSION OF EXOGENOUS GENES VIA AN ECDYSONE RECEPTOR COMPLEX

(75) Inventors: Glenn Richard Carlson, North Wales; Dean Ervin Cress, Souderton; Tarlochan Singh Dhadialla, Chalfont; Robert Eugene Hormann, Philadelphia; Dat Phat Le, North Wales, all of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/315,451

(22) Filed: May 20, 1999

Related U.S. Application Data

(63) Continuation-in-part of application No. 09/210,010, filed on Dec. 11, 1998, now abandoned.
(60) Provisional application No. 60/089,546, filed on Jun. 17, 1998.

(51) Int. Cl.[7] .................. C12N 15/82; C07D 319/14; C07C 241/00
(52) U.S. Cl. .................. 435/468; 435/440; 549/366; 549/405; 549/436; 564/310
(58) Field of Search .................. 514/649, 664; 549/366, 436, 405; 564/310, 311; 800/278; 435/440, 468

(56) References Cited

U.S. PATENT DOCUMENTS 5,530,028 * 6/1996 Lidert et al. .................. 514/649

FOREIGN PATENT DOCUMENTS

WO 96/27673 * 9/1996 (WO) .
WO 96/37609 * 11/1996 (WO) .

OTHER PUBLICATIONS

Yao, T–P. et al., "Functional Ecdysone Receptor is the Product of EcR and Ultraspiracle Genes," *Nature*, vol. 366, pp. 476–479, 1993.
Yao, T–P. et al., "Drosophila Ultraspiracle Modulates Ecdysone Receptor Function via Heterodimer Formation," *Cell*, vol. 71, pp. 63–72, 1992.
No, D. et al., "Ecdysone–Inducible Gene Expression in Mammalian Cells and Transgenic Mice," *Proc. Natl. Acad. Sci. USA*, vol. 93, pp. 3346–3351, 1996.
Trisyono et al. (1997) Effect of the nonsteroidal ecdysone agonists, methoxyfenozide and tebufenozide, on the European Corn Borer (Lepidoptera: Pyralidae). J. Econ. Entomol. 90:1486–1492, Dec. 1997.*

* cited by examiner

Primary Examiner—Robert A. Schwartzman
(74) Attorney, Agent, or Firm—Thomas D. Rogerson

(57) ABSTRACT

This invention relates to an improved method to modulate exogenous gene expression in which an ecdysone receptor complex comprising: a DNA binding domain; a ligand binding domain; a transactivation domain; and a ligand is contacted with a DNA construct comprising: the exogenous gene and a response element; wherein the exogenous gene is under the control of the response element and binding of the DNA binding domain to the response element in the presence of the ligand results in activation or suppression of the gene. The improvement resides in a select group of nonsteroid ligands which show improved activity over known ligands.

13 Claims, No Drawings

LIGANDS FOR MODULATING THE EXPRESSION OF EXOGENOUS GENES VIA AN ECDYSONE RECEPTOR COMPLEX

This application is a continuation in part of U.S. Ser. No. 09/210,010, filed Dec. 11, 1998, abandoned, which claims the benefit of U.S. Provisional Application No. 60/089,546, filed Jun. 17, 1998.

This invention relates to non-steroidal ligands which are useful for inducing or suppressing the expression of an exogenous gene in animal and plant cells.

In the field of genetic engineering, precise temporal control of gene expression, that is, the ability to activate or suppress a gene, is a valuable tool in studying, manipulating, and controlling development and other physiological processes (see, for example, Evans and No, PCT International Application No. PCT/US97/05330 and references cited therein). In mammalian systems, applications include inducible gene targeting, overexpression of toxic and teratogenic genes, anti-sense RNA expression, and gene therapy. In plant systems, applications include the control of plant traits, male or female fertility; overexpression of plant protective agents; and production of or modification of desired plant products including both native and non-native materials. For both animals and plants, inducibility can be valuable for foreign protein production, for example, therapeutic proteins, industrial enzymes, polymers, and the like.

It is important that the agent used to control gene expression, which is often referred to as a "gene switch", be one which is normally absent from the organism in which the gene to be controlled resides. This is to avoid unexpected expression or suppression of the gene. For example, an inducible tetracycline regulated system has been devised and utilized in transgenic mice whereby gene activity is induced in the absence of the antibiotic and suppressed in its presence. Unfortunately, in this case, the pharmacokinetics of tetracycline may interfere with its use as an efficient "on-off" gene switch.

International Patent Application No. PCT/GB96/01195 describes an insect steroid receptor isolated from *Heliothis virescens* ("HEcR") which is capable of acting as a gene switch responsive to both steroid (e.g., 20-hydroxyecdysone and Muristerone A) and certain non-steroidal inducers. Non-steroidal inducers have a distinct advantage over steroids, in this and many other systems which are responsive to both steroids and non-steroid inducers, for a number of reasons including, for example: lower manufacturing cost, metabolic stability, absence from insects, plants, or mammals, and environmental acceptability. The PCT application describes the utility of two dibenzoylhydrazines, 1,2-dibenzoyl-1-tert-butyl-hydrazine and tebufenozide (N-(4-ethylbenzoyl)-N'-(3,5-dimethylbenzoyl)-N'-tert-butyl-hydrazine) as gene switches for the HEcR system and suggests that other dibenzoylhydrazines, such as those disclosed in U.S. Pat. No. 5,117,057 may also function as gene switches in the system. While this may be true, activity of these dibenzoyl-hydrazines is uncertain. Specifically, U.S. Pat. No. 5,117,057 shows a very broad class of dibenzoylhydrazines, many of which appear to be ineffective as gene switches. GB96/01195 indicates that when 20 such dibenzoylhydrazines were tested, only 7 showed any activity.

International Patent Application No. PCT/EP96/00686 discloses the use of tebufenozide as a chemical ligand for the ecdysone receptor from *Drosophila melanogaster*. This receptor is used to control gene expression in transgenic plants resulting in the control of various traits of agronomic importance Unfortunately, even though the ligands described in the above-identified references show reporter gene induction activity in isolated cells, no consideration was made for their use in whole organisms such as intact plants, and animals.

Therefore, there remains a continuing need to develop non-steroidal ligands with increased or consistent activity compared to known ligands and which demonstrate that activity in intact plants and animals. We have discovered a limited group of dibenzoylhydrazine derivatives which not only show reporter gene induction activity in isolated cells but also have advantages over the known diacylhydrazines, 1,2-dibenzoyl-1-tert-butyl-hydrazine and tebufenozide, when used in intact plants and animals, due to their improved transport and distribution properties, metabolic stability, residual activity, affinity for the receptor, and lack of adverse effects.

This invention relates to an improvement in a method to modulate exogenous gene expression comprising contacting an ecdysone receptor complex comprising:

a) a DNA binding domain;

b) a ligand binding domain;

c) a transactivation domain; and d) a ligand;

with a DNA construct comprising:

a) the exogenous gene; and b) a response element;

wherein:

a) the exogenous gene is under the control of the response element; and b) binding of the DNA binding domain to the response element in the presence of the ligand results in activation or suppression of the gene;

the improvement comprising:

selecting the ligand from a compound of formula I:

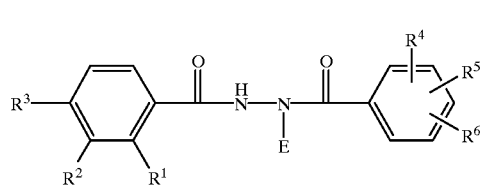

wherein:

E is a $(C_4-C_6)$alkyl containing a tertiary carbon or a cyano$(C_3-C_5)$alkyl containing a tertiary carbon;

$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, OMe, OEt, cyclopropyl, $CF_2CF_3$, CH═CHCN, allyl, azido, SCN, or $SCHF_2$;

$R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, Ac, F, Cl, OH, OMe, OEt, O-n-Pr, OAc, $NMe_2$, $NEt_2$, SMe, SEt, $SOCF_3$, $OCF_2CF_2H$, COEt, cyclopropyl, $CF_2CF_3$, CH═CHCN, allyl, azido, $OCF_3$, $OCHF_2$, O-i-Pr, SCN, $SCHF_2$, SOMe, NH—CN, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^4$, $R^5$, and $R^6$ are independently H, Me, Et, F, Cl, Br, formyl, $CF_3$, $CHF_2$, $CHCl_2$, $CH_2F$, $CH_2Cl$, $CH_2OH$, CN, C≡CH, 1-propynyl, 2-propynyl, vinyl, OMe, OEt, SMe, or SEt;

provided that:

a) when $R^1$ is Me and $R^2$ is OMe;
then $R^3$ is H; and the combination $R^4$, $R^5$, and $R^6$ is 3,5-di-Me, 3,5-di-OMe-4-Me, 3,5-di-Cl, or 3,5-di-F;

b) when $R^1$ is Me and $R^2$ is OEt;
then $R^3$ is H and the combination $R^4$, $R^5$, and $R^6$ is 3,5-di-Me, 3,5-di-OMe-4-Me, 3,5-di-Cl, 3,5-di-F, 2,4- or 2,5-di-F, 2,4- or 2,5-di-Cl;

c) when $R^1$ is Et and $R^2$ is OMe or OEt;
then $R^3$ is H and the combination $R^4$, $R^5$, and $R^6$ is:
  i) 3,5-di-OMe-4-Me, 3,5-di-Cl, 3,5-di-F, 2,4- or 2,5-di-F, 2,4- or 2,5-di-Cl, 3-OMe, 2-Cl-5-Me, 2-Br-5-Me, 2-Cl, 2-Br, or 3-Me; or
  ii) $R^6$ is H, $R^4$ is Me, and $R^5$ is Et, F, Cl, Br, formyl, $CF_3$, $CHF_2$, $CHCl_2$, $CH_2F$, $CH_2Cl$, $CH_2OH$, CN, C≡CH, 1-propynyl, 2-propynyl, vinyl, OMe, OEt, SMe, or SEt;

d) when $R^1$ is i-Pr;
then $R^2$ is OMe, or OEt; $R^3$ is H; and the combination $R^4$, $R^5$, and $R^6$ is 3,5-di-Me;

e) when $R^3$ is Et;
then $R^2$ is H, $R^1$ is F or Cl, and the combination $R^4$, $R^5$, and $R^6$ is 3,5-di-Me;

f) when $R^2$ and $R^3$, together with the phenyl carbons to which they are attached, form an ethylenedioxy ring;
then $R^1$ is Me or Et and the combination $R^4$, $R^5$, and $R^6$ is 3,5-di-Me;

g) when $R^2$ and $R^3$, together with the phenyl carbons to which they are attached, form a dihydrofuryl or dihydropyryl ring;
then $R^1$ is Et and the combination $R^4$, $R^5$, and $R^6$ is 3,5-di-Me;

h) when $R^1$ is formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, cyclopropyl, $CF_2CF_3$, CH=CHCN, allyl, azido, SCN, or $SCHF_2$;
then $R^2$ is OMe or OEt, $R^3$ is H, and the combination $R^4$, $R^5$, and $R^6$ is 3,5-di-Me; and i) when $R^2$ is Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, Ac, F, Cl, OH, O-n-Pr, OAc, $NMe_2$, $NEt_2$, SMe, SEt, $SOCF_3$, $OCF_2CF_2H$, COEt, cyclopropyl, $CF_2CF_3$, CH=CHCN, allyl, azido, $OCF_3$, $OCHF_2$, O-i-Pr, SCN, $SCHF_2$, SOMe, or NH—CN;
then $R^1$ is Et, $R^3$ is H, the combination $R^4$, $R^5$, and $R^6$ is 3,5-di-Me.

This invention also relates to a method to modulate exogenous gene expression comprising contacting an ecdysone receptor complex comprising:

a) a DNA binding domain;
b) a ligand binding domain;
c) a transactivation domain; and
d) a ligand consisting of a compound of formula I:

with a DNA construct comprising:
a) the exogenous gene; and
b) a response element;
wherein:
a) the exogenous gene is under the control of the response element; and
b) binding of the DNA binding domain to the response element in the presence of the ligand results in activation or suppression of the gene.

In order to achieve an optimum balance between a) ligand binding and the resulting gene switch activity, and b) transport, systemicity, toxicity, and metabolic stability in intact plants and animals, the position and size of the compound of formula I substituent groups are important. The optimum balance of properties appears to occur when E is t-butyl, $R^1$ is ethyl, $R^2$ is ethoxy, $R^3$ is hydrogen, and the combination $R^4$, $R^5$, and $R^6$ is 3,5-dimethyl. The composition of each of these "R" groups may be varied considerably. However, variations which lead to significant changes in the size, shape, and overall polarity of the compound of formula I will tend to reduce the optimum balance and, consequently, the improved properties of the compound. For this reason, when the composition of any one particular R group is changed from the optimum, variations in the composition of the remaining R groups should be limited.

Preferably, E is $(C_4-C_5)$alkyl. More preferably, E is t-butyl.

Preferably, $R^1$ is Me, Et, i-Pr, F, $CF_3$, $CHF_2$, $CHCl_2$, $CH_2F$, $CH_2Cl$, $CH_2OH$, $CH_2OMe$, $CH_2CN$, CN, C≡CH, or $CF_2CF_3$. More preferably, $R^1$ is Me, Et, i-Pr, F, $CF_3$, $CHF_2$, $CH_2F$, $CH_2OMe$, $CH_2CN$, C≡CH, or $CF_2CF_3$. Even more preferably, $R^1$ is Me, Et, i-Pr, or F. Most preferably, $R^1$ is Me or Et.

Preferably, $R^2$ is Et, $CF_3$, $CHF_2$, $CHCl_2$, $CH_2F$, $CH_2Cl$, $CH_2OH$, $CH_2OMe$, $CH_2CN$, CN, OH, OMe, OEt, O-n-Pr, $CF_2CF_3$, azido, $OCF_3$, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon. More preferably, $R^2$ is Et, $CF_3$, $CHF_2$, $CHCl_2$, $CH_2F$, $CH_2Cl$, $CH_2OH$, $CH_2OMe$, $CH_2CN$, CN, OH, OMe, OEt, $CF_2CF_3$, or joined with $R^3$ and the phenyl carbons to which $R^2$ and $R_3$ are attached to form an ethylenedioxy or dihydrofuryl ring with the oxygen adjacent to a phenyl carbon. Even more preferably, $R^2$ is OH, OMe, OEt, or joined with $R^3$ and the phenyl carbons to which $R^2$ and $R^3$ are attached to form an ethylenedioxy or dihydrofuryl ring with the oxygen adjacent to a phenyl carbon. Most preferably, $R^2$ is OMe or OEt.

Preferably, $R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon More preferably, $R^3$ is H, Et or joined with $R^2$ and the phenyl carbons to which $R^2$ and $R^3$ are attached to form an ethylenedioxy or dihydrofuryl ring with the oxygen adjacent to a phenyl carbon. Even more preferably, $R^3$ is joined with $R^2$ and the phenyl carbons to which $R^2$ and $R^3$ are attached to form an ethylenedioxy or dihydrofuryl ring with the oxygen adjacent to a phenyl carbon.

Preferably, $R^4$, $R^5$, and $R^6$ are independently Me, F, Cl, $CH_2OH$, or OMe. More preferably, $R^4$, $R^5$, and $R^6$ are independently Me, F, Cl, $CH_2OH$, or OMe. Even more preferably, $R^4$, $R^5$, and $R^6$ are independently Me, F, or Cl. Still more preferably, the combination of $R^4$, $R^5$, and $R^6$ is 3,5-di-Me, 3,5-di-Cl, or 3,5-di-F⁻. Most preferably, the combination of $R^4$, $R^5$, and $R^6$ is 3,5-di-Me.

The terms "Me", "Et", "n-Pr", "i-Pr", and "Ac" mean methyl, ethyl, normal propyl, isopropyl, and acetyl, respectively. When referring to $R^4$, $R^6$, and $R^6$, the term "2,4", "2,5", "3,5", and the like refer to the relative positions on the phenyl ring to which the groups are attached.

The term "halo" means fluoro, chloro, bromo, or iodo.

The term "modulate" means the ability of a given ligand/receptor complex to induce or suppress the transactivation of an exogenous gene.

The term "exogenous gene" means a gene foreign to the subject, that is, a gene which is introduced into the subject through a transformation process or an unmutated version of an endogenous mutated gene. The method of transformation is not critical to this invention and may be any method suitable for the subject known to those in the art. For example, transgenic plants are obtained by regeneration from the transformed cells. Numerous transformation procedures are known from the literature such as agroinfection using *Agrobacterium tumefaciens* or its $T_1$ plasmid, electroporation, microinjection of plant cells and protoplasts, and microprojectile transformation. Complementary techniques are known for transformation of animal cells and regeneration of such transformed cells in transgenic animals. Exogenous genes can be either natural or synthetic genes and therapeutic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject. The term "therapeutic gene" means a gene which imparts a beneficial function to the host cell in which such gene is expressed. Therapeutic genes are not naturally found in host cells.

The term "ecdysone receptor complex" generally refers to a heterodimeric protein complex consisting of two members of the steroid receptor family, ecdysone receptor ("EcR") and ultraspiracle ("USP") proteins (see Yao, T. P., et. al. (1993) Nature 366, 476–479; Yao, T.-P., et. al., (1992) Cell 71, 63–72). The functional ecdysteroid receptor complex may also include additional protein(s) such as immunophilins. Additional members of the steroid receptor family of proteins, known as transcriptional factors (such as DHR38, betaFTZ-1 or other insect homologs), may also be ligand dependent or independent partners for EcR and/or USP. The ecdysone receptor complex can also be a heterodimer of ecdysone receptor protein and the vertebrate homolog of ultraspiracle protein, retinoic acid-X-receptor ("RXR") protein. Homodimer complexes of the ecdysone receptor protein or USP may also be functional under some circumstances.

An ecdysteroid receptor complex can be activated by an active ecdysteroid or non-steroidal ligand bound to one of the proteins of the complex, inclusive of EcR, but not excluding other proteins of the complex.

The ecdysone receptor complex includes proteins which are members of the steroid receptor superfamily wherein all members are characterized by the presence of an amino-terminal transactivation domain, a DNA binding domain ("DBD"), and a ligand binding domain ("LBD") separated by a hinge region. Some members of the family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The term "response element" ("RE") means one or more cis-acting DNA elements which confer responsiveness on a promoter mediated through interaction with the DNA-binding domains of the ecdysone receptor complex. This DNA element may be either palindromic (perfect or imperfect) in its sequence or composed of sequence motifs or half sites separated by a variable number of nucleotides. The half sites can be similar or identical and arranged as either direct or inverted repeats. The ecdysone receptor complex binds, in the presence or absence of a ligand, to the DNA sequence of an RE to initiate or suppress transcription of downstream gene(s) under the regulation of this response element. Examples of DNA sequences for RE of the natural ecdysone receptor are known in the art (Cherbas L., et al., (1991), *Genes Dev.*, 5, 120–131; D'Avino P P., et al., (1995), *Mol. Cell. Endocrinol.*, 113, 1–9; Antoniewski C., et al., (1994), *Mol. Cell. Biol.*, 14, 4465–4474).

The DNA sequences making up the exogenous gene, the response element, and the ecdysone receptor complex may be incorporated into procaryotic cells such as *Escherichia coli, Bacillus subtilis*, or other enterobacteria. However, because many of the proteins expressed by the gene are processed incorrectly in bacteria, eucaryotic cells are preferred. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands for the ecdysone receptor. As a result, they are insensitive to the ligands of this invention. Thus, the ligands of this invention will have negligible physiological or other effects on transformed cells, or the whole organism. Therefore, cells can grow and express the desired product, substantially unaffected by the presence of the ligand itself.

The term "subject" means an intact plant or animal or a cell from a plant or animal. It is also anticipated that the ligands will work equally well when the subject is a fungus or yeast. When the subject is an intact animal, preferably the animal is a vertebrate, most preferably a mammal.

The ligands of the present invention, when used with the ecdysone receptor complex which in turn is bound to the response element linked to an exogenous gene, provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of the ecdysone receptor complex to a specific control, or regulatory, DNA element. The ecdysone receptor protein, like other members of the steroid receptor family, possesses at least three domains, a transactivation domain, a DNA binding domain, and a ligand binding domain. This receptor, like a subset of the steroid receptor family, also possesses less well defined regions responsible for heterodimerization properties. Binding of the ligand to the ligand binding domain of ecdysone receptor protein, after heterodimerization with USP or RXR protein, enables the DNA binding domains of the heterodimeric proteins to bind to the response element in an activated form, thus resulting in expression or suppression of the exogenous gene. This mechanism does not exclude the potential for ligand binding to either EcR or USP, and the resulting formation of active homodimer complexes (e.g. EcR+EcR or USP+USP). Preferably, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et. al. (1988) Nature, 335, 563–564) or LexA protein from E. coli (see Brent and Ptashne (1985), Cell, 43, 729–736) to accommodate chimeric ecdysone receptor complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. The term "promoter" means a specific nucleotide sequence recognized by RNA polymerase. The sequence is the site at which transcription can be specifically initiated under proper conditions. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cells) or specific to certain developmental stages of the organism.

Another aspect of this invention is a method to modulate the expression of one or more exogenous genes in an organism, comprising administering to the organism an effective amount, that is, the amount required to elicit the desired gene expression or suppression, of a ligand comprising a compound of formula I and wherein the cells of the organism contain:

a) an ecdysone receptor complex comprising:
      1) a DNA binding domain;
      2) a binding domain for the ligand; and
      3) a transactivation domain; and
   b) a DNA construct comprising:
      1) the exogenous gene; and
      2) a response element; and
wherein:
   a) the exogenous gene is under the control of the response element; and
   b) binding of the DNA binding domain to the response element in the presence of the ligand results in activation or suppression of the gene.

A related aspect of this invention is a method for regulating endogenous or heterologous gene expression in a transgenic organism comprising contacting a ligand comprising a compound of formula I with an ecdysone receptor within the cells of the organism wherein the cells contain a DNA binding sequence for the ecdysone receptor and wherein formation of an ecdysone receptor-ligand-DNA binding sequence complex induces expression of the gene.

A fourth aspect of the present invention is a method for producing a polypeptide comprising the steps of:

a) selecting a cell which is substantially insensitive to exposure to a ligand comprising a compound of formula I;
   b) introducing into the cell:
      1) a DNA construct comprising:
         a) an exogenous gene encoding the polypeptide; and
         b) a response element;
      wherein the gene is under the control of the response element; and 2) an ecdysone receptor complex comprising:
         a) a DNA binding domain;
         b) a binding domain for the ligand; and
         c) a transactivation domain; and
   c) exposing the cell to the ligand.

As well as the advantage of temporally controlling polypeptide production by the cell, this aspect of the invention provides a further advantage, in those cases when accumulation of such a polypeptide can damage the cell, in that expression of the polypeptide may be limited to short periods. Such control is particularly important when the exogenous gene is a therapeutic gene. Therapeutic genes may be called upon to produce polypeptides which control needed functions, such as the production of insulin in diabetic patients. They may also be used to produce damaging or even lethal proteins, such as those lethal to cancer cells. Such control may also be important when the protein levels produced may constitute a metabolic drain on growth or reproduction, such as in transgenic plants.

Numerous genomic and cDNA nucleic acid sequences coding for a variety of polypeptides are well known in the art. Exogenous genetic material useful with the ligands of this invention include genes that encode biologically active proteins of interest, such as, for example, secretory proteins that can be released from a cell; enzymes that can metabolize a substrate from a toxic substance to a non-toxic substance, or from an inactive substance to an active substance; regulatory proteins; cell surface receptors; and the like. Useful genes also include genes that encode blood clotting factors, hormones such as insulin, parathyroid hormone, luteinizing hormone releasing factor, alpha and beta seminal inhibins, and human growth hormone; genes that encode proteins such as enzymes, the absence of which leads to the occurrence of an abnormal state; genes encoding cytokines or lymphokines such as interferons, granulocytic macrophage colony stimulating factor, colony stimulating factor-1, tumor necrosis factor, and erythropoietin; genes encoding inhibitor substances such as $alpha_1$-antitrypsin, genes encoding substances that function as drugs such as diphtheria and cholera toxins; and the like. Useful genes also include those useful for cancer therapies and to treat genetic disorders. Those skilled in the art have access to nucleic acid sequence information for virtually all known genes and can either obtain the nucleic acid molecule directly from a public depository, the institution that published the sequence, or employ routine methods to prepare the molecule.

For gene therapy use, the ligands described herein may be taken up in pharmaceutically acceptable carriers, such as, for example, solutions, suspensions, tablets, capsules, ointments, elixirs and injectable compositions. Pharmaceutical preparations may contain from 0.01% to 99% by weight of the ligand. Preparations may be either in single or multiple dose forms. The amount of ligand in any particular pharmaceutical preparation will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being treated and may vary with factors such as the condition of the recipient.

The ligands described herein may also be administered in conjunction with other pharmaceutically active compounds. It will be understood by those skilled in the art that pharmaceutically active compounds to be used in combination with the ligands described herein will be selected in order to avoid adverse effects on the recipient or undesirable interactions between the compounds. Examples of other pharmaceutically active compounds which may be used in combination with the ligands include, for example, AIDS chemotherapeutic agents, amino acid derivatives, analgesics, anesthetics, anorectal products, antacids and antiflatulents, antibiotics, anticoagulants, antidotes, antifibrinolytic agents, antihistamines, anti-inflamatory agents, antineoplastics, antiparasitics, antiprotozoals, antipyretics, antiseptics, antispasmodics and anticholinergics, antivirals, appetite suppressants, arthritis medications, biological response modifiers, bone metabolism regulators, bowel evacuants, cardiovascular agents, central nervous system stimulants, cerebral metabolic enhancers, cerumenolytics, cholinesterase inhibitors, cold and cough preparations, colony stimulating factors, contraceptives, cytoprotective agents, dental preparations, deodorants, dermatologicals, detoxifying agents, diabetes agents, diagnostics, diarrhea medications, dopamine receptor agonists, electrolytes, enzymes and digestants, ergot preparations, fertility agents, fiber supplements, antifungal agents, galactorrhea inhibitors, gastric acid secretion inhibitors, gastrointestinal prokinetic agents, gonadotropin inhibitors, hair growth stimulants, hematinics, hemorrheologic agents, hemostatics, histamine $H_2$ receptor antagonists, hormones, hyperglycemic agents, hypolipidemics, immunosuppressants, laxatives, leprostatics, leukapheresis adjuncts, lung surfactants, migraine preparations, mucolytics, muscle relaxant antagonists, muscle relaxants, narcotic antagonists, nasal sprays, nausea medications nucleoside analogues, nutritional supplements, osteoporosis preparations, oxytocics, parasympatholytics, parasympathomimetics, Parkinsonism drugs, Penicillin adjuvants, phospholipids, platelet inhibitors, porphyria agents, prostaglandin analogues, prostaglandins, proton pump inhibitors, pruritus medications psychotropics, quinolones, respiratory stimulants, saliva stimulants, salt substitutes, sclerosing agents, skin wound preparations, smoking cessation aids, sulfonamides, sympatholytics, thrombolytics, Tourette's syndrome agents, tremor preparations, tuberculosis preparations, uricosuric agents, urinary tract agents, uterine contractants, uterine relaxants, vaginal preparations, vertigo agents, vitamin D analogs, vitamins, and medical imaging contrast media. In some cases the ligands may be useful as an adjunct to drug therapy, for example, to "turn off" a gene that produces an enzyme that metabolizes a particular drug.

For agricultural applications, in addition to the applications described above, the ligands of this invention may also be used to control the expression of pesticidal proteins such as *Bacillus thuringiensis* (Bt) toxin. Such expression may be tissue or plant specific. In addition, particularly when control of plant pests is also needed, one or more pesticides may be combined with the ligands described herein, thereby providing additional advantages and effectiveness, including fewer total applications, than if the pesticides are applied separately. When mixtures with pesticides are employed, the relative proportions of each component in the composition will depend upon the relative efficacy and the desired application rate of each pesticide with respect to the crops, pests, and/or weeds to be treated. Those skilled in the art will recognize that mixtures of pesticides may provide advantages such as a broader spectrum of activity than one pesticide used alone. Examples of pesticides which can be combined in compositions with the ligands described herein include fungicides, herbicides, insecticides, miticides, and biocides.

The ligands described herein can be applied to plant foliage as aqueous sprays by methods commonly employed, such as conventional high-liter hydraulic sprays, low-liter sprays, air-blast, and aerial sprays. The dilution and rate of application will depend upon the type of equipment employed, the method and frequency of application desired, and the ligand application rate. It may be desirable to include additional adjuvants in the spray tank, Such adjuvants include surfactants, dispersants, spreaders, stickers, antifoam agents, emulsifiers, and other similar materials described in *McCutcheon's Emulsifiers and Detergents, McCutcheon's Emulsifiers and Detergents/Functional Materials, and McCutcheon's Functional Materials*, all published annually by McCutcheon Division of MC Publishing Company (New Jersey). The ligands can also be mixed with fertilizers or fertilizing materials before their application. The ligands and solid fertilizing material can also be admixed in mixing or blending equipment, or they can be incorporated with fertilizers in granular formulations. Any relative proportion of fertilizer can be used which is suitable for the crops and weeds to be treated. The ligands described herein will commonly comprise from 5% to 50% of the fertilizing composition. These compositions provide fertilizing materials which promote the rapid growth of desired plants, and at the same time control gene expression.

The ligands of this invention are known compounds or are easily prepared by one skilled in the art adapting the procedures described in U.S. Pat. Nos. 5,117,057, 5,530,028, and 5,378,726. A two step process is typically used. In the first step, a substituted benzoic acid chloride of formula II is combined with a substituted hydrazine of formula III to give a monoacylhydrazine of formula IV. The monoacylhydrazine of formula IV is combined in a second step with another benzoic acid chloride of formula V resulting in formation of a compound of formula I.

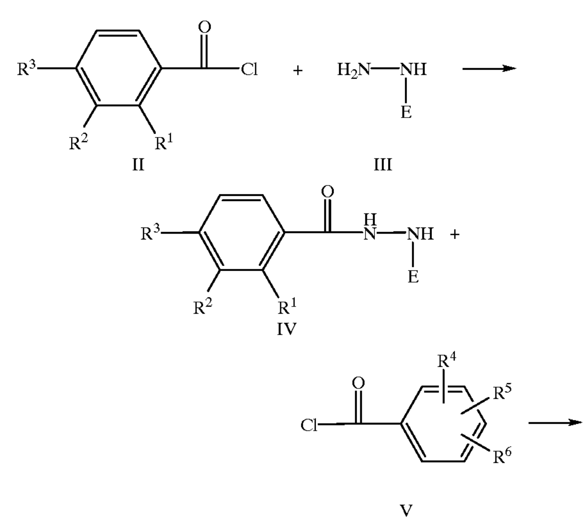

II III IV V

The following examples demonstrate the activity of the ligands of this invention.

The following ligands and comparative ligands were evaluated:

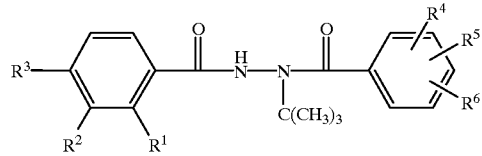

| Ligand | R1 | R2 | R3 | 3-R4 | 5-R5 | 4-R6 |
|---|---|---|---|---|---|---|
| CE-1 | H | H | Et | Me | Me | |
| CE-2 | H | H | H | H | H | |
| CE-3 | | | | | | |
| 1 | Et | OMe | H | OMe | H | |
| 2 | Me | —OCH₂CH₂O— | | Me | Me | |
| 3 | Me | OMe | H | Me | Me | |
| 4 | Et | OMe | H | F | F | |
| 5 | Et | OMe | H | Me | Me | |
| 6 | Me | OEt | H | Me | Me | |
| 7 | Et | —OCH₂CH₂O— | | Me | Me | |
| 8 | Et | —CH₂CH₂O— | | Me | Me | |
| 9 | Me | OMe | H | Cl | Cl | |
| 10 | Et | OMe | H | Cl | Me | |
| 11 | i-Pr | OMe | H | Me | Me | |
| 12 | Et | OEt | H | Me | Me | |
| 13 | Et | OMe | H | Cl | Cl | |
| 14 | Me | OH | H | Me | Me | |
| 15 | Me | OH | H | Me | CH2OH | |
| 17 | F | H | Et | Me | Me | |
| 18 | Me | OMe | H | OMe | OMe | Me |

CE-1 = tebufenozide
CE-2 = 1,2-dibenzoyl-1-tert-butyl-hydrazine
CE-3 = muristerone A Gene Constructs pVgRXR (Invitrogen Corp., Carlsbad, Calif.) is an 8728 kb plasmid that expresses both VgEcR and RXR to form a modified heterodimeric nuclear receptor (see No, D., et. al., (1996) Proc. Natl. Acad. Sci. USA, 93, 3346–3351). The ecdysone receptor (VgEcR) is derived from the natural Drosophila ecdysone receptor and modified to contain the VP16 transactivation domain (see Cress, W. D., and Triezenberg, S. J. (1991), Science 251, 87–90; Sadowski, I., et. al (1988) Nature 335, 563–564; Triezenberg, S. Jet. al., (1988), Genes Dev 2, 718–729; Triezenberg, S. J., et. al., (1988), Genes Dev 2, 730–742). RXR is the mammalian homologue of USP (ultraspiracle), the natural partner to the Drosophila ecdysone receptor (see Yao, T.-P., et. al., (1993), Nature 366, 476–479; Yao, T.-P., et. al., (1992), Cell 71, 63–72). The P-box region of the VgEcR DNA binding domain was modified to recognize the hybrid ecdysone response element that consists of one half-site from the gluccorticoid response element (see Umesono, K., and Evans, R. M. (1989), Cell 57, 1139–1146) and one half-site from the natural ecdysone response element. This hybrid response element reduces any possible interaction with the farsenoid X receptor that may bind the natural ecdysone responsive element (EcRE). The cytomegalovirus enhancer-promoter drives expression of VgEcR, and the Rous sarcoma virus promoter drives expression of RXR. The vector pIND (Invitrogen Corp.) is a 5024 bp vector based on pcDNA3.1. It contains five hybrid E/GREs recognized by the modified ecdysone receptor expressed from pVgRXR and a minimal heat shock promoter (see Yao, T. P., et. al., (1993), Nature, 366, 476–479). pIND/lacZ (Invitrogen Corp.) is a 8170 bp plasmid that contains the β-galactosidase gene as a reporter enzyme. Cotransfection of pIND/lacZ and pVgRXR results in the induction of β-galactosidase expression upon addition of ecdysone agonists such as muristerone A. The reporter plasmid pIND/luc was constructed by subcloning the firefly luciferase gene from pGL3 (Promega/E1741) as a Nhe I-BamHI fragment into pIND, also digested with Nhe I and BamHI.

Maintenance of Mammalian Cell Lines and Transfection

CHO cells (ATCC #CCL-61) were maintained in F-12 Nutrient mixture (Ham's media) (Gibco/BRL, 11765-054) supplemented with 10% fetal bovine serum (FBS, complete medium; Gibco/BRL, 16000-036). These cells were maintained at 37° C. in 5% $CO_2$ in 95% atmospheric air.

The CHO cells were seeded into 12-well tissue culture plates at a concentration of $0.5 \times 10^5$ cells per ml per well. The lipid Pfx-8 (Invitrogen, T930-18) was used to transiently transfect the ecdysone inducible expression system (Invitrogen catalog number K1000-01). The ecdysone inducible expression system consists of pVgRXR, encoding the receptor subunits, and pIND/lacZ or pIND/luc, containing the response element and a reporter gene encoding β-galactosidase or luciferase respectively. Twenty-four hours after seeding cells, the lipid/DNA solution was prepared by 0.5 mg/ml of VgRXR and 0.5 mg/ml pIND/lacZ or pIND/luc DNAs in sterile water. Thirty-six µl of Pfx-8 was diluted in a sterile 17×100 mm polystyrene tube containing 1.5 ml Opti-MEM medium (Gibco/BRL, 31985). Six µl of the plasmid DNA stock was mixed with 1.5 ml of Opti-MEM medium in another polystyrene tube. The DNA and the lipid solutions were combined to make 3 ml of transfection solution (enough for one set of triplicate samples). Cells were washed with phosphate buffered solution (PBS; Gibco/BRL, 14190-144) three times by aspirating medium from the cells. One ml transfection solution was added per well. Cells were incubated for four hours, and the transfection medium replaced with the same volume of complete medium. Cells were incubated for an additional 20 hours.

Stably Transformed Mammalian Cell Line

CHO cells stably transformed with pVgRXR and pIND/LacZ(SPI) (Invitrogen Corp.) were maintained in Hams F-12 media containing 10% FBS, 2 mM glutamine, 300 µg/ml Zeocin (Invitrogen Corp.) and 300 µg/ml Hygromycin B. pIND(SPI), an alternative to the pIND vector, can be induced to absolute expression levels five-fold greater than that of pIND due to the presence of 3 cis-acting SPI elements. Basal expression levels are correspondingly greater.

Treatment with Ligands

Stock solutions ($10^{-2}$ M) were prepared for muristerone A and the non-steroidal ligands of the present invention in ethanol and acetone respectively, and stored at −20° C. Twenty-four hours after transfection, a test compound was added at a final concentration of 10 µM ($10^{-5}$ M) to each 1 ml cell culture well. Muristerone A (Sigma, M7888), at 10 µM concentration was used as a positive control. Acetone alone was added as a negative control.

Reporter Gene Assays

Reporter gene expression was evaluated 24–48 hours after treatment of transiently transfected cells or 24 hours after treatment of the stably transformed cell line with test ligands. β-galactosidase was assayed by either staining fixed cells or assaying for enzymatic activity in cellular lysates. β-galactosidase catalyzes the hydrolysis of the β-galactoside, X-gal (5-bromo-4-chloro-3-indolyl-β-galactopyranoside) producing a blue color within the fixed cells (Invitrogen, K1465-01) that can be visualized under a microscope. Alternatively, reporter lysis buffer (RLB; Promega/E397A) was used to lyse the cells for the detection of β-galactosidase activity using a chemiluminescent substrate, Galacto-Star (Tropix/BM100S). The cells within each 12-well plate were lysed with 250 µl of RLB. Twenty µl of each extract was assayed with 100 µl of substrate.

For detection of luciferase activity, cells were washed twice with PBS and lysed with 250 µl RLB per well. After 10 minutes, the plate was frozen at −80° C. for 10 minutes and returned to room temperature. A 20 µl sample of lysate was mixed with 100 µl luciferase assay reagent (Promega, E1500). For both β-galactosidase and luciferase assays, luminescence was detected at room temperature using a DYNEX MLX microtiter plate luminometer equipped with an autoinjector for the delivery of the substrate.

Cytosolic Ecdysone Receptor Extract Preparation from Drosophila Kc Cells

The dipteran cell line Kc167, originally derived from Drosophila embryos (see Echalier, G. and Ohanessian, A. (1969) C. R. Acad. Sci., 268, 1771) was obtained from Dr. Peter Cherbas (Indiana University) and maintained as described (Cherbas, L., et. al., (1994), Methods in Cell Biology, 44, 161–179). A 400 ml culture of Kc cells ($3\times10^7$ cells per ml) was centrifuged at 700×g for 10 minutes at room temperature to pellet the cells. The supernatant was aspirated and the pellet was resuspended in 70 ml of cold TM buffer (10 mM Tris, 5 mM $MgCl_2$, 1 mM DTT, pH 7.2). After a 10 minute incubation on ice, the cells were centrifuged at 2,300×g. The supernatant was discarded. The cell pellet was frozen at −20° C. for 1 hour. The frozen cell pellet was thawed slowly on ice and homogenized in a cold Potter-Elvehjem homogenizer using a teflon pestle on a Caframo homogenizer motor, at setting 500 with 10 up and down strokes at 4° C. This slurry was centrifuged at 100,000×g in a swinging bucket rotor for 60 minutes. The supernatant, containing the cytosolic protein extract was diluted with T buffer (10 mM Tris, 1 mM DTT, pH 7.2) to a protein concentration of 5 mg/ml. This extract was used immediately for ligand binding assays.

Nuclear Ecdysone Receptor Preparation from *Plodia interpunctella* Cells

The cell line IAL-PID2, derived from imaginal wing discs of the lepidopteran *Plodia interpunctella* was obtained from H. Oberlander and maintained as described (Lynn, E. E. and Oberlander, H., (1983), J. Insect Physiology, 29, 591–96). A 300 ml stationary phase culture of *P. interpunctella* cells was centrifuged at 700×g for 10 min at room temperature to pellet the cells. The supernatant was aspirated and the cellular pellet resuspended in 35 ml TMT (TM buffer with 0.1% Triton X-100). The suspension was homogenized with twenty up and down strokes of a Dounce homogenizer on ice. Homogenate was incubated on ice for 10 minutes and then centrifuged for 15 min at 900×g. The pellet was resuspended in 15 ml TM buffer and centrifuged at 2,300×g. This pellet was extracted in TMK buffer (TM buffer with 800 mM KCl) by using a glass rod to crush the pellet until a gelatinous slurry was formed and incubated on ice for 15 minutes. The extract was centrifuged at 100,000×g in a swinging bucket rotor for 60 minutes. The supernatant, which constituted the nuclear extract, was desalted on a 10 DG desalting column (Bio-Rad, 732-2010) equilibrated with T-buffer. The total protein concentration in the nuclear extract was adjusted to 5 mg per ml with T-buffer containing 1 mM DTT.

Bacterial Glutathion-S-transferase Fusion Protein Preparation

Bacterial glutathion-S-transferase (GST) fusion proteins of the spruce budworm (*Choristoneura fumiferana*) EcR (CfEcR), containing CDEF domains only, and ultraspiracle protein (CfUSP) were also used in radioligand displacement assays. cDNA encoding the CDEF domains of CfEcR were constructed following PCR amplification using primers that contain BamH1 and EcoRI sites (Perera S C, M Sundaram, Krell P J, Retnakaran A, Dhadialla T S, S R Palli, 1999 *Arch. Insect Biochem. Physiol.* 41, In Press). The PCR product was digested with BamHI and EcoRI and cloned into pGEX-3X vector obtained from Pharmacia Biotech. CfUSP coding region was amplified using primers that contain BamHl and EcoRI sites and cloned into to pGEX-2T vector obtained from Pharmacia Biotech. *E. coli* transformed with each of the two vectors were grown and induced to produce the fusion proteins as detailed in the Pharmacia Biotech GST-technical bulletin.

Ecdysone Receptor Competitive Binding Assay $^3H$ ponasterone A, a potent phytoecdysteroid, (66,000 dpm; specific activity 170 Ci/mmole; NEN Life Science Products, Boston, Mass.) was mixed with 100 µl Kc cytosolic or Plodia nuclear ecdysone receptor extracts in 0.8×50 mm glass test tubes in the absence or presence of 10 µM unlabelled 20-hydroxyecdysone (20E) to obtain an estimate of total or non-specific, respectively, binding of tritiated ponasterone A. The tubes were vortexed and incubated overnight at 4° C. for Kc cytosolic extracts or 1.5 hours for Plodia nuclear extracts for binding reactions to reach equilibrium. At the end of equilibrium binding times, the bound tritiated ponasterone A was separated from the unbound by addition of ice-cold 600 µl or 300 µl dextran-coated charcoal solution (500 mg of Sigma HCL-washed activated charcoal, 50 mg Pharmacia Dextran T70, 50 ml T-buffer) to Kc or Plodia extracts, respectively. The tubes were vortexed briefly and centrifuged at 7,000×g to pellet the charcoal. The supernatant, 600 µl or 300 µl for Kc or Plodia extract reactions, respectively, containing tritiated ponasterone A bound to proteins, was aspirated into liquid scintillation vials containing 5 ml scintillation cocktail (ReadySafe®, Beckmann) each. The mixture was vortexed and the amount of total or non-specifically bound radioactivity measured in a Beckman LS500 liquid scinitllation counter with a 60% counting efficiency for tritium.

Determination of Kd Values for Competitive Inhibitors of $^3H$-ponasterone A Binding to Ecdysteroid Receptor Complexes in Kc or Plodia Cell Extracts and Bacterial Fusion Proteins The concentrations of competitors that inhibited 50% of tritiated ponasterone A binding ($IC_{50}$) was determined by incubating Kc or Plodia nuclear extracts or extracts of bacteria producing CfEcR(CDEF-GST and CfUSP-GST fusions proteins with $^3H$-ponasterone A (66,000 dpm per reaction) in the presence of a range of concentrations (0.1 nM to 10 µM) of test compounds. In the case of binding reactions using bacterial fusion proteins, 20 or one µl extract of bacteria producing CfEcR(CDEF)-GST or CfUSP-GST fusion proteins, respectively, were included per binding reaction. The assay conditions and determination of total and non-specific binding was as described above. The volume of competitor in solvent, like that for 20E or solvent alone, was kept at 1% of total reaction volume by using a 100 fold concentrated stock solution (i.e. a 100 fold dilution of stock solutions). The remainder of the assay was as described above. Each reaction was carried out in duplicate per concentration per test compound. Specific binding of $^3$H-ponasterone A was determined by subtracting non-specific binding (that obtained in the presence of 10 μM 20E) from total (no competitor) or competed radioactivity bound. The data for each (test compound was analyzed using IGOR Pro software (WaveMetrics, Lake Oswego, Oreg.) to calculate IC$_{50}$ values. The binding constant (K$_d$ in μM) for the test compounds was calculated by incorporating the Cheng-Prusoff equation (see Munson P J. and Rodbard D. (1980) *Anal. Biochem.* 107, 220–239) in the IGOR Pro software.

Tables 1–3 summarize the data obtained:

TABLE 1

| Ligand | Kg log(1/EC50) | Plodia log(1/IC50) | Bacterial CfECR log(1/IC50) |
|---|---|---|---|
| CE-1 | 6.55 | 8.7 | |
| CE-2 | 5.52 | 6.48 | |
| CE-3 | 7.96 | | |
| 1 | 7.36 | 8.52 | |
| 2 | 7.16 | 9.14 | |
| 3 | 6.73 | 9.04 | 8.76 |
| 4 | 7.41 | 8.51 | |
| 5 | 7.70 | 9.49 | |
| 6 | | 8.82 | |
| 7 | | 8.78 | |
| 8 | | 8.85 | |
| 9 | | 9.00 | |
| 10 | | 8.80 | |
| 11 | | 8.93 | |
| 12 | 8.10 | 9.63 | |
| 13 | 7.44 | 9.06 | |
| 14 | | | 8.61 |
| 15 | | | 8.49 |
| 17 | | 9.24 | |
| 18 | | 8.82 | |

TABLE 2

Luciferase Gene Activation in Transiently Transfected CHO Cells

| Ligand 10 μM | Luciferase activity[1] | Induction Ratio[2] | Kd for Kc cells (nM) |
|---|---|---|---|
| none | 42 | | |
| CE-1 | 89 | 2 | 110 |
| CE-2 | 36 | 1 | 2000 |
| CE-3 | 316 | 8 | 2.3 |
| CE-4 | 418 | 10 | 0.7 |
| 1 | 275 | 7 | 39.5 |
| 2 | 204 | 5 | 60 |
| 3 | 324 | 8 | 124 |
| 4 | 251 | 6 | 47 |
| 5 | 313 | 8 | 13.3 |
| 12 | 305 | 7 | 5.3 |
| 13 | 226 | 5 | 65 |

CE-4 = ponasterone A
[1]In relative light units (RLU) - Average of duplicate samples
[2]Ratio of RLU in presence and absence of the ligand

TABLE 3

β-Galactosidase Gene Activation in Stably Transformed CHO Cells

| Ligand 10 mM | β-Galactosidase activity[1] | Induction Ratio[2] | Kd for Kc cells (nM) |
|---|---|---|---|
| none | 200 | | |
| CE-1 | 323 | 2 | 192 |
| CE-2 | 145 | 1 | 2000 |
| CE-3 | 9830 | 49 | 2 |
| CE-4 | 10386 | 52 | 0.7 |

TABLE 3-continued

β-Galactosidase Gene Activation in Stably Transformed CHO Cells

| Ligand 10 mM | β-Galactosidase activity[1] | Induction Ratio[2] | Kd for Kc cells (nM) |
|---|---|---|---|
| 1 | 1123 | 6 | 40 |
| 2 | 536 | 3 | 47 |
| 3 | 681 | 3 | 124 |
| 4 | 1963 | 10 | 26 |
| 5 | 11599 | 58 | 13 |
| 12 | 9830 | 49 | 5 |
| 13 | 6667 | 33 | 24 |

[1]In relative light units (RLU) - Average of triplicate samples
[2]Ratio of RLU in presence and absence of the ligand These data indicate that the ligands of this invention are able to induce gene expression at concentrations comparable to or less than those of the known compounds CE-1 and CE-2.

In addition to improved gene expression modulation capabilities, the ligands are expected to have greater utility in intact plants and animals due to their superior transport and metabolic properties. The following example demonstrates the improved plant transport of a ligand of this invention (Ligand 3) compared to a known ligand (CE-1) in plants.

Translaminar Movement

A study was conducted to evaluate translaminar movement of two compounds into cotton leaves using neonate beet armyworm larvae, *Spodoptera exigua*, as the model system.

Two treatments were evaluated: emulsifiable concentrates of CE-1 and Ligand 3 (5% and 19%, respectively), at a concentration of 100 μg/ml to simulate spray tank concentrations. These treatments were then compared with plants treated with a chemical standard known to have excellent translaminar movement (emamectin benzoate, 0.16% EC [20 μg/ml], Merck & Co.) and with nontreated plants.

Four-week-old cotton, *Gossypium hirsutum* L. cv. Stoneville, plants were treated with each treatment by painting the top surface of a single replicate leaf/plant with a corresponding treatment. Plants were held in a controlled-environment glasshouse maintained at 27° C. until needed. Residual effectiveness was evaluated by challenging treated and nontreated foliage with neonate beet armyworm larvae, *Spodoptera exigua* (Hübner), on 3 dates: 1, 7, and 14 days after treatment (DAT). On each sample date, the single treated leaf/plant was excised from each of five replicate plants per treatment. Leaves were then fastened to the top lid of a plastic Petri dish (100×20 mm) and then infested with 10 first instar larvae. First instar beet armyworm larvae commonly feed on the under surface of leaves and generally do not feed all the way through to the upper surface. Thus translaminar movement of material would be necessary to affect the larvae since the compounds were applied to the leaf top-surface only. Mortality of larvae was recorded 4 days after infestation. In addition, any live larvae were observed for symptoms characteristic of molt accelerating compounds (formation of new cuticle and/or slipped head capsule). Each treatment was replicated five times.

Percentage mortality data were transformed to the arcsine of the square-root and then analyzed by ANOVA using JMP (Ver. 3.2.1). Means were separated by the Tukey-Kramer test (P=0.05).

Results showed that Ligand 3 was significantly more effective than CE-1 at killing *S. exigua* larvae from translaminar movement and, therefore, would be expected to have hig c) a transactivation domain; and
d) a ligand of the formula:

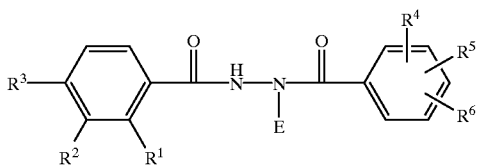

wherein:

E is a $(C_4-C_6)$alkyl containing a tertiary carbon or a cyano$(C_3-C_5)$alkyl containing a tertiary carbon;

$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, OMe, OEt, cyclopropyl, $CF_2CF_3$, CH=CHCN, allyl, azido, SCN, or $SCHF_2$;

$R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, Ac, F, Cl, OH, OMe, OEt, O-n-Pr, OAc, $NMe_2$, $NEt_2$, SMe, SEt, $SOCF_3$, $OCF_2CF_2H$, COEt, cyclopropyl, $CF_2CF_3$, CH=CHCN, allyl, azido, $OCF_3$, $OCHF_2$, O-i-Pr, SCN, $SCHF_2$, SOMe, NH—CN, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^4$, $R^5$, and $R^6$ are independently H, Me, Et, F, Cl, Br, formyl, $CF_3$, $CHF_2$, $CHCl_2$, $CH_2F$, $CH_2Cl$, $CH_2OH$, CN, C≡CH, 1-propynyl, 2-propynyl, vinyl, OMe, OEt, SMe, or SEt;

provided that:

a) when $R^1$ is Me and $R^2$ is OMe;
then $R^3$ is H; and the combination $R^4$, $R^5$, and $R^6$ is 3,5-di-Me, 3,6-di-OMe-4-Me, 3,5-di-Cl, or 3,5-di-F;

b) when $R^1$ is Me and $R^2$ is OEt;
then $R^3$ is H and the combination $R^4$, $R^5$, and $R^6$ is 3,5-di-Me, 3,5-di-OMe-4-Me, 3,5-di-Cl, 3,5-di-F, 2,4- or 2,5-di-F, 2,4- or 2,5-di-Cl;

c) when $R^1$ is Et and $R^2$ is OMe or OEt;
then $R^3$ is H and the combination $R^4$, $R^5$, and $R^6$ is:
i) 3,5-di-OMe-4-Me, 3,5-di-Cl, 3,5-di-F, 2,4- or 2,5-di-F, 2,4- or 2,5-di-Cl, 3-OMe, 2-Cl-5-Me, 2-Br-5-Me, 2-Cl, 2-Br, or 3-Me; or
ii) $R^6$ is H, $R^4$ is Me, and $R^5$ is Et, F, Cl, Br, formyl, $CF_3$, $CHF_2$, $CHCl_2$, $CH_2F$, $CH_2Cl$, $CH_2OH$, CN, C≡CH, 1-propynyl, 2-propynyl, vinyl, OMe, OEt, SMe, or SEt;

d) when $R^1$ is i-Pr;
then $R^2$ is OMe, or OEt; $R^3$ is H; and the combination $R^4$, $R^5$, and $R^6$ is 3,5-di-Me;

e) when $R^3$ is Et;
then $R^2$ is H, $R^1$ is F or Cl, and the combination $R^4$, $R^5$, and $R^6$ is 3,5-di-Me;

f) when $R^2$ and $R^3$, together with the phenyl carbons to which they are attached, form an ethylenedioxy ring;
then $R^1$ is Me or Et and the combination $R^4$, $R^5$, and $R^6$ is 3,5-di-Me;

g) when $R^2$ and $R^3$, together with the phenyl carbons to which they are attached, form a dihydrofuryl or dihydropyryl ring;
then $R^1$ is Et and the combination $R^4$, $R^5$, and $R^6$ is 3,5-di-Me;

h) when $R^1$ is formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, cyclopropyl, $CF_2CF_3$, CH=CHCN, allyl, azido, SCN, or $SCHF_2$;
then $R^2$ is OMe or OEt, $R^3$ is H, and the combination $R^4$, $R^5$, and $R^6$ is 3,5-di-Me; and i) when $R^2$ is Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, Ac, F, Cl, OH, O-n-Pr, OAc, $NMe_2$, $NEt_2$, SMe, SEt, $SOCF_3$, $OCF_2CF_2H$, COEt, cyclopropyl, $CF_2CF_3$, CH=CHCN, allyl, azido, $OCF_3$, $OCHF_2$, O-i-Pr, SCN, $SCHF_2$, SOMe, or NH—CN;
then $R^1$ is Et, $R^3$ is H, the combination $R^4$, $R^5$, and $R^6$ is 3,5-di-Me;

with a DNA construct comprising:
a) the exogenous gene; and
b) a response element;

wherein:
a) the exogenous gene is under the control of the response element; and
b) binding of the DNA binding domain to the response element in the presence of the ligand results in activation or suppression of the gene.

3. The method of claim 2 wherein the ligand is of the specified formula and E is t-butyl; $R^1$ is Me, Et, i-Pr, or F; $R^2$ is OH, OMe, OEt, or joined with $R^3$ and the phenyl carbons to which $R^2$ and $R^3$ are attached to form an ethylenedioxy or dihydrofuryl ring with the oxygen adjacent to a phenyl carbon; $R^3$ is H, Et or joined with $R^2$ and the phenyl carbons to which $R^2$ and $R^3$ are attached to form an ethylenedioxy or dihydrofuryl ring with the oxygen adjacent to a phenyl carbon; and $R^4$, $R^5$, and $R^6$ are independently Me, F, Cl, $CH_2OH$, or OMe.

4. The method of claim 2 wherein the ligand is of the specified formula and E is t-butyl, $R^1$ is Et, $R^2$ is OEt, $R^3$ is H, and the combination $R^4$, $R^5$, and $R^6$ is 3,5-di-Me.

5. The method of claim 2 wherein the ecdysone receptor complex is a chimeric ecdysone receptor complex and the DNA construct further comprises a promoter.

6. A method to modulate the expression of one or more exogenous genes in a plant, comprising administering to the plant an effective amount of a ligand of the formula:

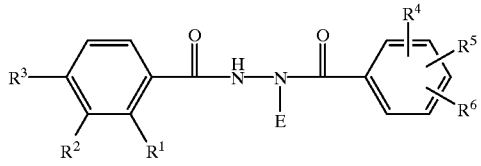

wherein:

E is a $(C_4-C_6)$alkyl containing a tertiary carbon or a cyano$(C_3-C_5)$alkyl containing a tertiary carbon;

$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, OMe, OEt, cyclopropyl, $CF_2CF_3$, CH=CHCN, allyl, azido, SCN, or $SCHF_2$;

$R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, Ac, F, Cl, OH, OMe, OEt, O-n-Pr, OAc, NMe$_2$, NEt$_2$, SMe, SEt, SOCF$_3$, OCF$_2$CF$_2$H, COEt, cyclopropyl, CF$_2$CF$_3$, CH=CHCN, allyl, azido, OCF$_3$, OCHF$_2$, O-i-Pr, SCN, SCHF$_2$, SOMe, NH—CN, or joined with R$^3$ and the phenyl carbons to which R$^2$ and R$^3$ are attached to form an ethylenedioxy, a dihydrofuryl ring with the oxygen adjacent to a phenyl carbon, or a dihydropyryl ring with the oxygen adjacent to a phenyl carbon;

R$^3$ is H, Et, or joined with R$^2$ and the phenyl carbons to which R$^2$ and R$^3$ are attached to form an ethylenedioxy, a dihydrofuryl ring with the oxygen adjacent to a phenyl carbon, or a dihydropyryl ring with the oxygen adjacent to a phenyl carbon;

R$^4$, R$^5$, and R$^6$ are independently H, Me, Et, F, Cl, Br, formyl, CF$_3$, CHF$_2$, CHCl$_2$, CH$_2$F, CH$_2$Cl, CH$_2$OH, CN, C≡CH, 1-propynyl, 2-propynyl, vinyl, OMe, OEt, SMe, or SEt;

provided that:
a) when R$^1$ is Me and R$^2$ is OMe;
then R$^3$ is H; and the combination R$^4$, R$^5$, and R$^6$ is 3,5-di-Me, 3,5-di-OMe-4-Me, 3,5-di-Cl, or 3,5-di-F;
b) when R$^1$ is Me and R$^2$ is OEt;
then R$^3$ is H and the combination R$^4$, R$^5$, and R$^6$ is 3,5-di-Me, 3,5-di-OMe-4-Me, 3,5-di-Cl, 3,6-di-F, 2,4- or 2,5-di-F, 2,4- or 2,5-di-Cl;
c) when R$^1$ is Et and R$^2$ is OMe or OEt;
then R$^3$ is H and the combination R$^4$, R$^5$, and R$^6$ is:
  i) 3,5-di-OMe-4-Me, 3,5-di-Cl, 3,5-di-F, 2,4- or 2,5-di-F, 2,4- or 2,5-di-Cl, 3-OMe, 2-Cl-5-Me, 2-Br-5-Me, 2-Cl, 2-Br, or 3-Me; or
  ii) R$^6$ is H, R$^4$ is Me, and R$^5$ is Et, F, Cl, Br, formyl, CF$_3$, CHF$_2$, CHCl$_2$, CH$_2$F, CH$_2$Cl, CH$_2$OH, CN, C≡CH, 1-propynyl, 2-propynyl, vinyl, OMe, OEt, SMe, or SEt;
d) when R$^1$ is i-Pr;
then R$^2$ is OMe, or OEt; R$^3$ is H; and the combination R$^4$, R$^5$, and R$^6$ is 3,5-di-Me;
e) when R$^3$ is Et;
then R$^2$ is H, R$^1$ is F or Cl, and the combination R$^4$, R$^5$, and R$^6$ is 3,5-di-Me;
f) when R$^2$ and R$^3$, together with the phenyl carbons to which they are attached, form an ethylenedioxy ring;
then R$^1$ is Me or Et and the combination R$^4$, R$^5$, and R$^6$ is 3,5-di-Me;
g) when R$^2$ and R$^3$, together with the phenyl carbons to which they are attached, form a dihydrofuryl or dihydropyryl ring;
then R$^1$ is Et and the combination R$^4$, R$^5$, and R$^6$ is 3,5-di-Me;
h) when R$^1$ is formyl, CF$_3$, CHF$_2$, CHCl$_2$, CH$_2$F, CH$_2$Cl, CH$_2$OH, CH$_2$OMe, CH$_2$CN, CN, C≡CH, 1-propynyl, 2-propynyl, vinyl, OH, cyclopropyl, CF$_2$CF$_3$, CH=CHCN, allyl, azido, SCN, or SCHF$_2$;
then R$^2$ is OMe or OEt, R$^3$ is H, and the combination R$^4$, R$^5$, and R$^6$ is 3,5-di-Me; and
i) when R$^2$ is Me, Et, n-Pr, i-Pr, formyl, CF$_3$, CHF$_2$, CHCl$_2$, CH$_2$F, CH$_2$Cl, CH$_2$OH, CH$_2$OMe, CH$_2$CN, CN, C≡CH, 1-propynyl, 2-propynyl, vinyl, Ac, F, Cl, OH, O-n-Pr, OAc, NMe$_2$, NEt$_2$, SMe, SEt, SOCF$_3$, OCF$_2$CF$_2$H, COEt, cyclopropyl, CF$_2$CF$_3$, CH=CHCN, allyl, azido, OCF$_3$, OCHF$_2$, O-i-Pr, SCN, SCHF$_2$, SOMe, or NH—CN;
then R$^1$ is Et, R$^3$ is H, the combination R$^4$, R$^5$, and R$^6$ is 3,5-di-Me;

wherein the cells of the plant contain:
a) an ecdysone receptor complex comprising:
  1) a DNA binding domain;
  2) a binding domain for the ligand; and
  3) a transactivation domain; and
b) a DNA construct comprising:
  1) the exogenous gene; and
  2) a response element; and
wherein:
a) the exogenous gene is under the control of the response element; and
b) binding of the DNA binding domain to the response element in the presence of the ligand results in activation or suppression of the gene.

7. The method of claim 3 wherein the ligand is of the specified formula and E is t-butyl; R$^1$ is Me, Et, i-Pr, or F; R$^2$ is OH, OMe, OEt, or joined with R and the phenyl carbons to which R$^2$ and R$^3$ are attached to form an ethylenedioxy or dihydrofuryl ring with the oxygen adjacent to a phenyl carbon; R$^2$ is H, Et or joined with R$^2$ and the phenyl carbons to which R$^2$ and R$^3$ are attached to form an ethylenedioxy or dihydrofuryl ring with the oxygen adjacent to a phenyl carbon; and R$^4$, R$^5$, and R$^6$ are independently Me, F, Cl, CH$_2$OH, or OMe.

8. The method of claim 6 wherein the ligand is of the specified formula and E is t-butyl, R$^1$ is Et, R$^2$ is OEt, R$^3$ is H, and the combination R$^4$, R$^5$, and R$^6$ is 3,5-di-Me.

9. The method of claim 6 wherein the ecdysone receptor complex is a chimeric ecdysone receptor complex and the DNA construct further comprises a promoter.

10. A method for regulating endogenous or heterologous gene expression in a transgenic plant comprising contacting a ligand of the formula:

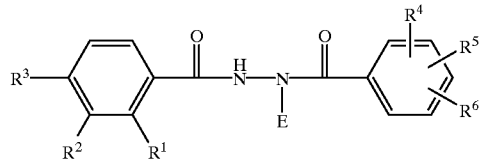

wherein:
E is a (C$_4$–C$_6$)alkyl containing a tertiary carbon or a cyano(C$_3$–C$_5$)alkyl containing a tertiary carbon;

R$^1$ is H, Me, Et, i-Pr, F, formyl, CF$_3$, CHF$_2$, CHCl$_2$, CH$_2$F, CH$_2$Cl, CH$_2$OH, CH$_2$OMe, CH$_2$CN, CN, C≡H, 1-propynyl, 2-propynyl, vinyl, OH, OMe, OEt, cyclopropyl, CF$_2$CF$_3$, CH=CHCN, allyl, azido, SCN, or SCHF$_2$;

R$^2$ is H, Me, Et, n-Pr, i-Pr, formyl, CF$_3$, CHF$_2$, CHCl$_2$, CH$_2$F, CH$_2$Cl, CH$_2$OH, CH$_2$OMe, CH$_2$CN, ON, C≡OH, 1-propynyl, 2-propynyl, vinyl, Ac, F, Cl, OH, OMe, OEt, O-n-Pr, OAc, NMe$_2$, NEt$_2$, SMe, SEt, SOCF$_8$, OCF$_2$CF$_2$H, COEt, cyclopropyl, CF$_2$CF$_3$, CH=CHCN, allyl, azido, OCF$_3$, OCHF$_2$, O-i-Pr, SON, SOHF$_2$, SOMe, NH—CN, or joined with R$^3$ and the phenyl carbons to which R$^2$ and R$^3$ are attached to form an ethylenedioxy, a dihydrofuryl ring with the oxygen adjacent to a phenyl carbon, or a dihydropyryl ring with the oxygen adjacent to a phenyl carbon;

R$^3$ is H, Et, or joined with R$^2$ and the phenyl carbons to which R$^2$ and R$^3$ are attached to form an ethylenedioxy, a dihydrofuryl ring with the oxygen adjacent to a phenyl carbon, or a dihydropyryl ring with the oxygen adjacent to a phenyl carbon;

$R^4$, $R^5$, and $R^6$ are independently H, Me, Et, F, Cl, Br, formyl, $CF_3$, $CHF_2$, $CHCl_2$, $CH_2F$, $CH_2Cl$, $CH_2OH$, CN, C≡CH, 1-propynyl, 2-propynyl, vinyl, OMe, OEt, SMe, or SEt;

provided that:
a) when $R^1$ is Me and $R^2$ is OMe;
then $R^3$ is H; and the combination $R^4$, $R^5$, and $R^6$ is 3,5-di-Me, 3,5-di-OMe-4-Me, 3,5-di-Cl, or 3,5-di-F;
b) when $R^1$ is Me and $R^2$ is OEt;
then $R^3$ is H and the combination $R^4$, $R^5$, and $R^6$ is 3,5-di-Me, 3,5-di-OMe-4-Me, 3,5-di-Cl, 3,5-di-F, 2,4- or 2,5-di-F, 2,4- or 2,5-di-Cl;
c) when $R^1$ is Et and $R^2$ is OMe or OEt;
then $R^3$ is H and the combination $R^4$, $R^5$, and R is:
i) 3,5-di-OMe-4-Me, 3,5-di-Cl, 3,5-di-F, 2,4- or 2,5-di-F, 2,4- or 2,5-di-Cl, 3-OMe, 2-Cl-5-Me, 2-Br-5-Me, 2-Cl, 2-Br, or 3-Me; or
ii) $R^6$ is H, $R^4$ is Me, and $R^5$ is Et, F, Cl, Br, formyl, $CF_3$, $CHF_2$, $CHCl_2$, $CH_2F$, $CH_2Cl$, $CH_2OH$, CN, C≡CH, 1-propynyl, 2-propynyl, vinyl, OMe, OEt, SMe, or SEt;
d) when $R^1$ is i-Pr;
then $R^2$ is OMe, or OEt; $R^3$ is H; and the combination $R^4$, $R^5$, and $R^6$ is 3,5-di-Me;
e) when $R^3$ is Et;
then $R^2$ is H, $R^1$ is F or Cl, and the combination $R^4$, $R^5$, and $R^6$, is 3,5-di-Me;
f) when $R^2$ and $R^3$, together with the phenyl carbons to which they are attached, form an ethylenedioxy ring;
then $R^1$ is Me or Et and the combination $R^4$, $R^5$, and $R^6$ is 3,5-di-Me;
g) when $R^2$ and $R^3$, together with the phenyl carbons to which they are attached, form a dihydrofuryl or dihydropyryl ring;
then $R^1$ is Et and the combination $R^4$, $R^5$, and $R^6$ is 3,5-di-Me;
h) when $R^1$ is formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, cyclopropyl, $CF_2CF_3$, CH=CHCN, allyl, azido, SCN, or $SCHF_2$;
then $R^2$ is OMe or OEt, $R^3$ is H, and the combination $R^4$, $R^5$, and $R^6$ is 3,5-di-Me; and
i) when $R^2$ is Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, Ac, F, Cl, OH, O-n-Pr, OAc, $NMe_2$, $NEt_2$, SMe, SEt, $SOCF_3$, $OCF_2CF_2H$, COEt, cyclopropyl, $CF_2CF_3$, CH=CHCN, allyl, azido, $OCF_3$, $OCHF_2$, O-i-Pr, SCN, $SCHF_2$, SOMe, or NH—CN;
then $R^1$ is Et, $R^3$ is H, the combination $R^4$, $R^5$, and $R^6$ is 3,5-di-Me;

with an ecdysone receptor complex within the cells of the plant wherein the cells further contain a DNA binding sequence for the ecdysone receptor complex when in combination with the ligand and wherein formation of an ecdysone receptor complex-ligand-DNA binding sequence complex induces expression of the gene.

11. The method of claim 10 wherein the ligand is of the specified formula and E is t-butyl; $R^1$ is Me, Et, i-Pr, or F; $R^2$ is OH, OMe, OEt, or joined with $R^3$ and the phenyl carbons to which $R^2$ and $R^3$ are attached to form an ethylenedioxy or dihydrofuryl ring with the oxygen adjacent to a phenyl carbon; $R^3$ is H, Et or joined with $R^2$ and the phenyl carbons to which $R^2$ and $R^3$ are attached to form an ethylenedioxy or dihydrofuryl ring with the oxygen adjacent to a phenyl carbon; and $R^4$, $R^5$, and $R^6$ are independently Me, F, Cl, $CH_2OH$, or OMe.

12. The method of claim 10 wherein the ligand is of the specified formula and E is t-butyl, $R^1$ is Et, $R^2$ is OEt, $R^3$ is H, and the combination $R^4$, $R^5$, and $R^6$ is 3,5-di-Me.

13. The method of claim 10 wherein the ecdysone receptor complex is a chimeric ecdysone receptor complex and the DNA construct further comprises a promoter.

* * * * *